United States Patent
Wong

(10) Patent No.: US 6,776,040 B2
(45) Date of Patent: Aug. 17, 2004

(54) SELF-LEVELING HYDROMETER

(76) Inventor: Tommy Chi-Kin Wong, Rm. 1901, Win Century Centre 2A, Mongkok Rd., Kowloon (HK)

( * ) Notice: Subject to any disclaimer, the term of this patent is extended or adjusted under 35 U.S.C. 154(b) by 0 days.

(21) Appl. No.: 10/374,078

(22) Filed: Feb. 27, 2003

(65) Prior Publication Data

US 2004/0060342 A1 Apr. 1, 2004

(30) Foreign Application Priority Data

Sep. 30, 2002 (CN) ........................ 02248510 U

(51) Int. Cl.$^7$ ................................. G01N 9/16
(52) U.S. Cl. ...................................... 73/454
(58) Field of Search ................. 73/32 R, 441, 73/450, 451, 454

(56) References Cited

U.S. PATENT DOCUMENTS

| | | | | |
|---|---|---|---|---|
| 2,282,069 A | * | 5/1942 | Linebarger | 73/454 |
| 2,296,169 A | * | 9/1942 | Linebarger | 73/454 |
| 2,674,120 A | * | 4/1954 | Trainor | 73/454 |
| 3,678,755 A | * | 7/1972 | Llucia | 73/454 |
| 3,722,292 A | * | 3/1973 | Pietramale | 73/454 |
| 4,037,481 A | * | 7/1977 | Callahan | 73/454 |
| 4,353,253 A | * | 10/1982 | Callahan | 73/454 |
| 4,697,454 A | * | 10/1987 | Lu | 73/440 |
| 5,631,420 A | * | 5/1997 | Wong | 73/454 |
| 6,561,026 B2 | * | 5/2003 | Tu | 73/454 |

FOREIGN PATENT DOCUMENTS

| CN | 96229010.6 | 12/1997 |
|---|---|---|
| CN | 01229324.5 | 5/2002 |

* cited by examiner

Primary Examiner—Hezron Williams
Assistant Examiner—John Hanley
(74) Attorney, Agent, or Firm—Rabin & Berdo, P.C.

(57) ABSTRACT

The present invention is a self-leveling hydrometer. A balance hanger is on top of a handle, which connects to a swinging support part. An imbalanced load is in the center of the floating measurement indicator and the imbalanced load can rotate freely in the round hole on the center of the floating measurement indicator. The imbalanced load has a protrudent round plate on edge that exposes on the round hole of the floating measurement indicator. A moveable hook, the support part and the imbalanced load can position the present invention in an absolute horizontal position for accurate liquid specific gravity readout. The present invention can also achieve easier and more accurate initial calibration process during manufacturing.

12 Claims, 5 Drawing Sheets

SELF-LEVELING HYDROMETER

BACKGROUND OF THE INVENTION

I. Field of the Invention

This invention relates generally to a self-leveling hydrometer and, more specifically, to a self-leveling hydrometer that automatically adjusts the hydrometer itself to an absolute horizontal position for accurate liquid specific gravity readout.

II. Description of the Prior Art

It is known that the proper adjustment of the specific gravity of saltwater is essential to the fish inside a saltwater fish tank. It is necessary to use a hydrometer to measure and adjust the proper specific gravity of the saltwater in a fish tank to equal that of actual seawater. Either adding salt or fresh water will conversely raise or lower the specific gravity of saltwater.

One of the prior arts listed in China patent No. 96229010.6 and No. 01229324.5, is a transparent container in a flat plastic shape fixed internally with a rotating floating plastic pointer that swings in an up and down arc. The pointer is weighted by a round disc to achieve accurate calibration. The end of the pointer points to a printed numerical specific-gravity chart etched on the outside of the plastic unit. When placed down into the fish tank, the water flows up from the bottom of the unit into an inner tube and then flows over and down into the measuring chamber. It is not necessary to put your hand in the water during the sample collection, thus avoiding the chance of contaminating the water in the tank. With the collected water sample in the chamber and the unit positioned in a perfectly horizontal position, the needle will float up to point to a number on the chart to indicate the specific gravity reading of the saltwater in the tank.

If the hydrometer is not held perfectly level, the specific gravity reading will be inaccurate. Therefore it is very difficult to hold the hydrometer level in order to take an accurate reading. Held in the hand, or set on a table that is not perfectly level, will yield inaccurate readings.

SUMMARY OF THE INVENTION

It is therefore a primary objective of the invention to provide an automatic, self-leveling hydrometer that can adjust itself to an absolute horizontal position to attain accurate specific gravity values of the saltwater.

In order to achieve the objective set forth, a self-leveling hydrometer in accordance with the present invention comprises a container with a floating measurement indicator or pointer. The container further has an upper hanging bracket that allows the container to swing freely to allow gravity to pull it to an absolute horizontal position while being held by hand or hung from a stationery hook.

An imbalanced load is in the center of the floating measurement indicator, the imbalanced load can rotate freely in the round hole on the center of the floating measurement indicator; the imbalanced load has a protrudent round plate on edge, the protrudent round plate exposes on the round hole of the floating measurement indicator.

The hidden tube has three inlets on following locations: a. on the bottom of the container, b. above the liquid level outside the measure chamber and c. on the bottom of the measure chamber.

BRIEF DESCRIPTION OF THE DRAWINGS

The accomplishment of the above-mentioned object of the present invention will become apparent from the following description and its accompanying drawings which disclose illustrative an embodiment of the present invention, and are as follows.

DESCRIPTION OF THE PREFERRED EMBODIMENT

Figure 1:
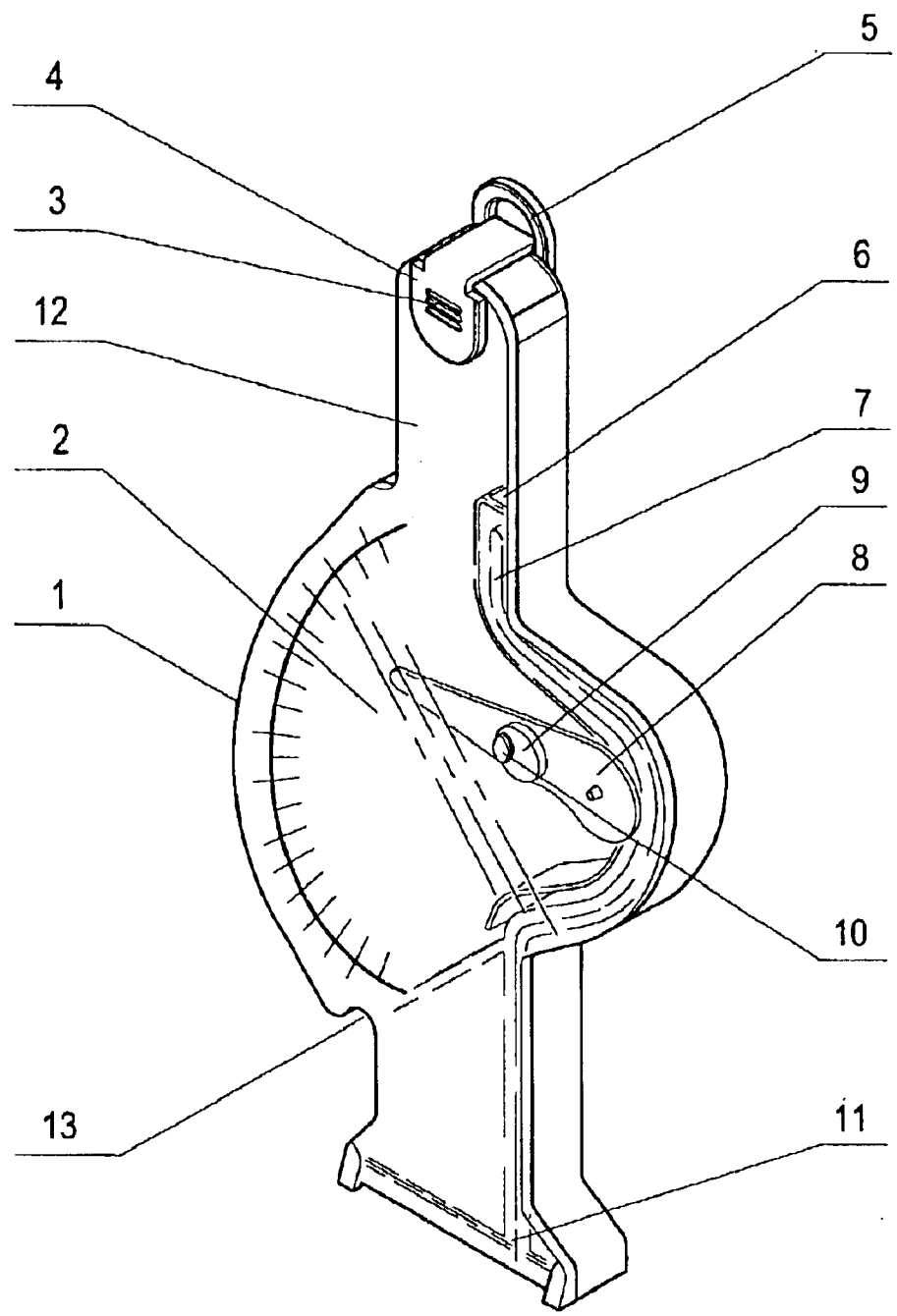
FIG. 1 is a perspective view of the present invention.
Figure 1A:
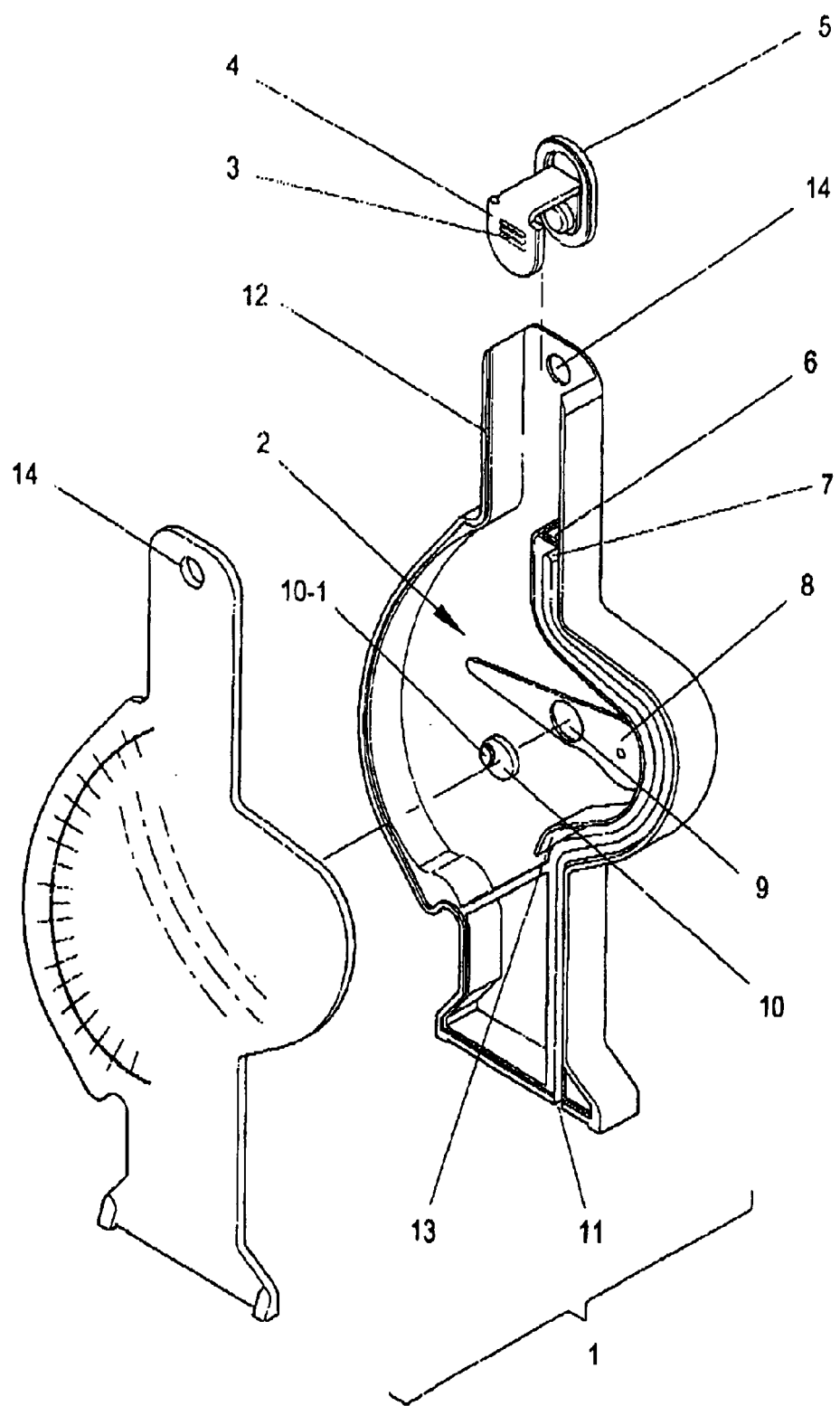
FIG. 1A is an exploded view of the present invention.
Figure 2:
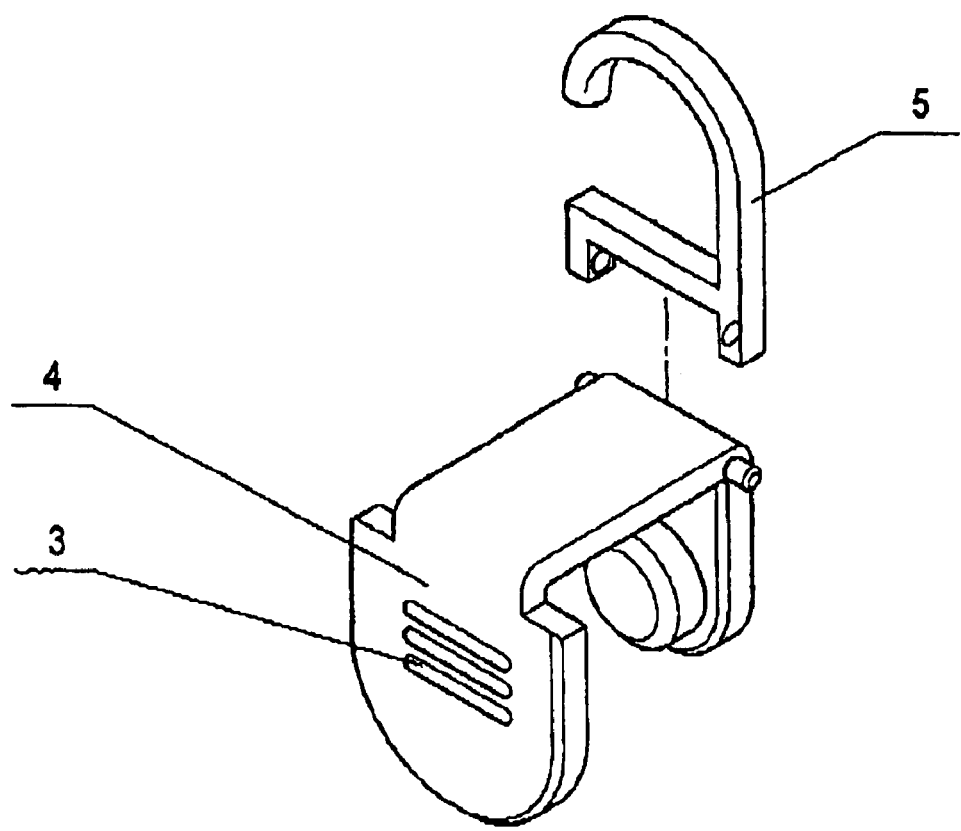
FIG. 2 is a perspective view of a support part of the present invention.

Referring to FIGS. 1 and 1A, the present invention is composed of a container (1), and a floating measurement indicator (8). The container (1) further includes an upper handle (12) and lower measure chamber (2). The measurement indicator (8) that swings freely is installed inside the measure chamber (2) of the container (1). A hidden tube (7) is on the inner wall of the container (1), the hidden tube (7) has three openings at the following locations: an opening (13) inside the measure chamber (2), an opening (6) above the liquid level outside the measure chamber, and an opening (11) on the bottom of the measure chamber. A balance hanger 14 is at a top of the handle (12). The balance hanger 14 connects to a swinging support part (4). A holding part (3) and a moveable hook (5) are on the support part (4). The moveable hook (5) is in inverted "U"-shape (FIG. 1) or a swingable question-mark shape (FIG. 2).

Figure 3:
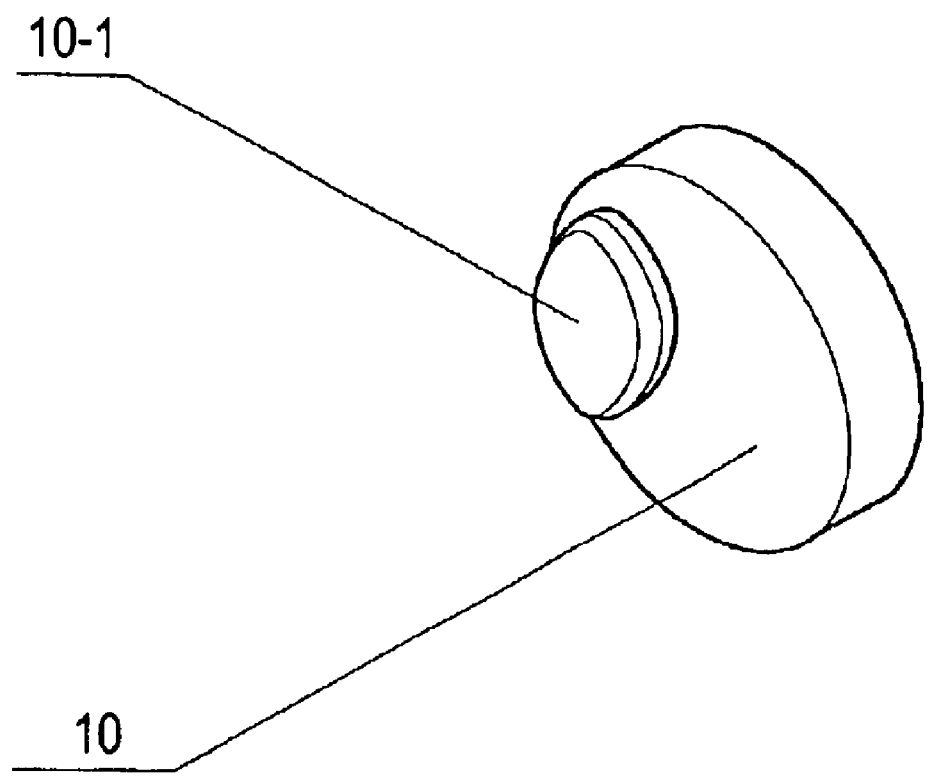
FIG. 3 is a perspective view of a further embodiment of the imbalanced load of the present invention.
Figure 4:
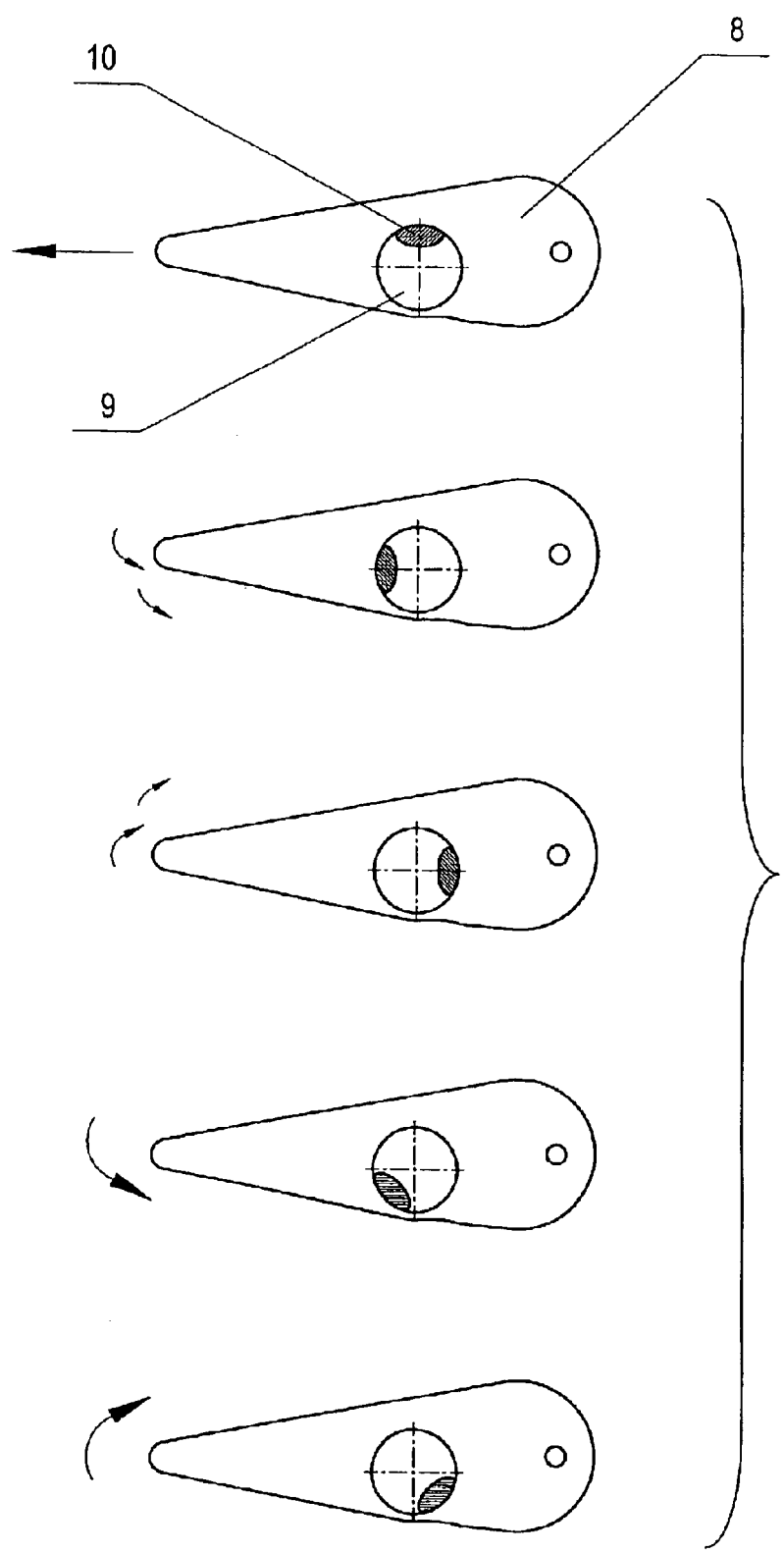
FIG. 4 is a perspective view of another embodiment in different locations of the imbalanced load in the round hole of the floating measurement indicator of the present invention.

An imbalanced load (10) is in the center of the floating measurement indicator (8). The imbalanced load (10) can rotate freely in a round hole (9) formed in the center of the floating measurement indicator (8). The imbalanced load (10) has a protrudent round plate (10-1) on its edge (as shown in FIG. 3). The protrudent round plate (10-1) projects from the round hole (9) of the floating measurement indicator (8). The imbalanced load (10) can rotate in the round hole (9), to allow the device to be calibrated, for example. By rotating the imbalanced load (10), the barycenter of the imbalanced load (10) is adjusted for the exact location of the floating measurement indicator (8) to get an accurate readout. The imbalanced load (10) can be made with a more dense material on an edge thereof for the imbalance effect.

The support part (4) has an elastic holding part (3). During measurement, users can hold the holding part (3) at a proper depth and angle to ensure measuring accuracy. After proper sampling, users can reduce the holding strength or hang the support part (4) from a solid fixture. The support part (4) will allow the container 1 to swing and sink to achieve an absolute horizontal position to ensure the measurement accuracy. Sea water flows into the inverted "U" shape hidden tube (7) from opening 11, and from opening (13) and into the measure chamber (2), while forcing air out of the hidden tube (7) through the opening (6). The sea water thus flows from a bottom of the container to a top of the container and then back down, i.e., from the bottom of the measure chamber (2) and into the measure chamber (2) to avoid introducing floating oil and protein bubbles from the water surface that might influence the floatation of the floating measurement indicator (8), so to ensure the accuracy and usage duration of the hydrometer. After sampling and removal from the seawater, the liquid in the hidden tube (7) can be poured from the opening (6) and from the upper handle (12). This arrangement also avoids the vacuum effect to prevent the siphoning of the water sample from the measure chamber (2).

While a preferred embodiment of the invention has been shown and described in detail, it will be readily understood and appreciated that numerous omissions, changes and additions may be made without departing from the spirit and scope of the invention.

What is claimed is:

1. A self-leveling hydrometer, comprising
   a container having an upper handle and lower measure chamber;
   a freely swingable floating measurement indicator disposed inside said measure chamber;
   a hidden tube arranged on an inner wall of said container, said hidden tube extending from a bottom of said lower measure chamber, to a first position above said floating measurement indicator, and being bent back downward at the first position to terminate at a second position disposed below said floating measurement indicator, so that said hidden tube has essentially an inverted U-shape, said hidden tube further having a first opening which communicates an inside of said hidden tube with an outside of said container to allow an introduction of a fluid into said hidden tube, a second opening disposed at the first position and which communicates the inside of said hidden tube with the inside of said measure chamber to allow air to enter and exit said hidden tube, and a third opening disposed at the second position and which communicates the inside of said hidden tube with the inside of said measure chamber, wherein when said hydrometer is positioned in fluid to measure a specific gravity of the fluid, the second opening is disposed above a level of the fluid, and the first and third openings are positioned below the level of the fluid; and
   a balance hanger disposed on top of said handle.

2. The self-leveling hydrometer recited in claim 1, wherein said balance hanger is connected to a swinging support part.

3. The self-leveling hydrometer recited in claim 2, wherein said swinging support part has a holding part.

4. The self-leveling hydrometer recited in claim 2, wherein said swinging support part has a moveable hook.

5. The self-leveling hydrometer recited in claim 4, wherein said moveable hook has an inverted U shape.

6. The self-leveling hydrometer recited in claim 1, wherein said moveable hook has a question-mark shape.

7. The self-leveling hydrometer recited in claim 1, wherein said floating measurement indicator has an imbalanced load positioned at a center thereof.

8. The self-leveling hydrometer recited in claim 7, wherein said floating measurement indicator has a round hole formed at the center, and said imbalanced load rotates in the round hole.

9. The self-leveling hydrometer recited in claim 8, wherein said imbalanced load has a protrudent round plate on an edge thereof, said protrudent round plate projecting out from said round hole of said floating measurement indicator.

10. The self-leveling hydrometer recited in claim 8, wherein said imbalanced load has an edge made with a dense material to provide for an imbalance effect.

11. The self-leveling hydrometer recited in claim 7, wherein said floating measurement indicator has a round hole formed at the center, and said imbalanced load has a protrudent round plate on an edge thereof, said protrudent round plate projecting out from said round hole of said floating measurement indicator.

12. The self-leveling hydrometer recited in claim 7, wherein said floating measurement indicator has a round hole formed at the center, and said imbalanced load has an edge made with a dense material to provide for an imbalance effect.

* * * * *